(12) United States Patent
Johdo et al.

(10) Patent No.: US 6,388,058 B1
(45) Date of Patent: May 14, 2002

(54) METHOD OF PURIFYING DAUNOMYCIN

(75) Inventors: Osamu Johdo, Fujisawa; Konomi Iguchi, Chigasaki; Takeo Yoshioka, Ayase, all of (JP)

(73) Assignee: Mercian Corporation, Tokyo (JP)

( * ) Notice: Subject to any disclaimer, the term of this patent is extended or adjusted under 35 U.S.C. 154(b) by 0 days.

(21) Appl. No.: 09/486,289

(22) PCT Filed: Aug. 25, 1998

(86) PCT No.: PCT/JP98/03767

§ 371 Date: Feb. 25, 2000

§ 102(e) Date: Feb. 25, 2000

(87) PCT Pub. No.: WO99/11650

PCT Pub. Date: Mar. 11, 1999

(30) Foreign Application Priority Data

Aug. 28, 1997 (JP) .............................................. 9-245980

(51) Int. Cl.⁷ .................................................. C07H 1/00
(52) U.S. Cl. ........................ 536/6.4; 536/16.9; 536/127
(58) Field of Search ................................ 536/6.5, 16.9, 536/127

(56) References Cited

U.S. PATENT DOCUMENTS

| 4,861,870 A | 8/1989 | Oppico et al. ............. 536/16.9 |
| 5,183,808 A | 2/1993 | Sawada et al. |

FOREIGN PATENT DOCUMENTS

| EP | 387 830 A2 | 9/1990 |
| EP | 387 830 A3 | 9/1990 |
| JP | 58-223062 | 12/1983 |
| JP | 7-252291 | 10/1995 |

OTHER PUBLICATIONS

G. Nicholls, "Solid–Phase extraction and optimized separation of doxorubicin, epirubicin and their metabolites using reversed–phase high–prformance liquid chromatography", Journal of Pharmaceutical Biomedical Analysis, vol. 10, Nos. 10–12, (1992), pp. 949–957.

*Primary Examiner*—Elli Peselev
(74) *Attorney, Agent, or Firm*—Wenderoth, Lind & Ponack, L.L.P.

(57) ABSTRACT

The present invention relates to a method in which daunomycin is eluted from a hydrophobic porous synthetic resin carrier onto which daunomycin is adsorbed from crude daunomycin with a buffered aqueous solution containing a water-miscible organic solvent to recover purified daunomycin. Daunomycin (daunorubicin) is purified efficiently.

10 Claims, 5 Drawing Sheets

METHOD OF PURIFYING DAUNOMYCIN

This application is a 371 of PCT/JP98/03767 filed Aug. 25, 1988.

TECHNICAL FIELD

The present invention relates to a purifying method for obtaining a high purity product of daunomycin which is an anthracycline antibiotic.

BACKGROUND ART

It is known that daunomycin (called as well daunorubicin) is obtained from a culture medium for ray fungus, and it is an anthracycline antibiotic which has a wide range anticancer spectrum against experimental tumor (refer to U.S. Pat. No. 3,616,242). As a matter of fact, it is widely used as a cancer chemotherapeutic agent for a clinical purpose.

Analogous anthracycline: antibiotics including daunomycin (hereinafter abbreviated as "DM") are further purified by treating products roughly purified from the culture medium described above with a cation exchange resin (for example, Amberlite™ IRC 50) and eluting them with a sodium chloride-containing aqueous solution or methanol containing sodium chloride (Japanese Patent Publication No. 44347/1974 and Japanese Patent Application Laid-Open No. 15880/1975). Further, published as well are methods comprising the steps of adsorbing the antibiotic described above onto a polymeric ion exchange resin (for example, Amberlite™ ER 180) or a CM Sepharose resin (for example, Sepharose™ CHB) and then eluting it with a mixture of acidic water and a polar solvent (Japanese Patent Application Laid-Open No. 118797/1984 and Japanese Patent Publication No. 39476/1992 originating therein, divisionally filed Japanese Patent Application Laid-Open No. 252291/1995, and U.S. Pat. No. 4,861,870 corresponding to them). Further, it is described as well in the latter official gazettes that a roughly purified anthracycline antibiotic is adsorbed onto an adsorptive porous synthetic resin carrier (for example, Amberlite™ XAD2) at a pre-purifying step before treating with the polymeric ion exchange resin described above, and the antibiotic described above is then eluted with a mixture of water/methanol (5:1) (v/v).

It seems that DM having a fixed high purity can be obtained according to the conventional adsorbing and eluting techniques described above. However, the more the high purity product is tried to obtain, the more the recovery percentage of intended DM is reduced. In contrast with this, the more the recovery percentage is tried to enhance, the more the purity of the product can not be elevated. In particular, when trying to recover DM from a culture medium, purified DM tends to be accompanied with impurities (for example, those having a longer retention time than that of DM in HPLC analysis which shall be described later) which are difficult to be removed at purifying steps including crystallization subsequent thereto.

Accordingly, an object of the present invention is to provide a purifying method in which high purity DM can be obtained from starting crude DM at a high yield in a simple manner.

DISCLOSURE OF THE INVENTION

The present inventors have found that DM having a high purity can be obtained at a high yield by using an adsorptive (or hydrophobic) synthetic resin carrier which is used at a preliminary purifying step prior to treatment using an ion exchange resin (for example, Amberlite™ ERI 180) for obtaining a high purity product and by selecting specific elution (or dissolution) conditions. It shall be quite surprising that the problems described above can be solved only by using a hydrophobic synthetic resin carrier which is merely used at a preliminary purifying step where an ion exchange resin is inevitably used in order to obtain a high purity product as described in, for example, Japanese Patent Application Laid-Open No. 118797/1984 described above.

Hence, according to the present invention, provided is a purifying method of daunomycin characterized by eluting daunomycin from a hydrophobic porous synthetic resin carrier onto which daunomycin is adsorbed from crude daunomycin with an aqueous solution which contains a water-miscible organic solvent and which is buffered to pH 2.5 to 6 and recovering purified daunomycin from the eluent.

Figure 1A:
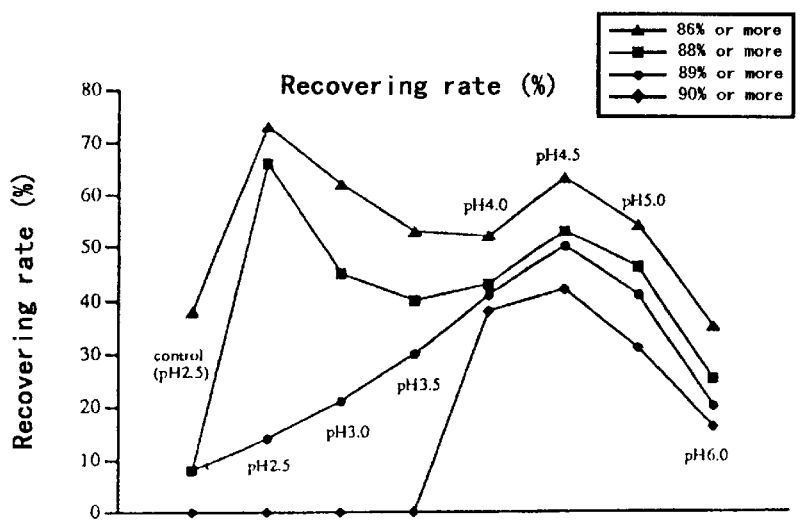
FIGS. 1A to 1C are graphs showing the recovery rates, the recovered liquid amounts and the relative purities of DM in Examples 1 to 8.

Control (pH 2.5), pH 2.5, pH 3.0, pH 3.5, pH 4.0, pH 4.5, pH 5.0 and pH 6.0 on the basis of an abscissa in the drawing correspond respectively to the results of Examples 1 to 8.

Figure 2:
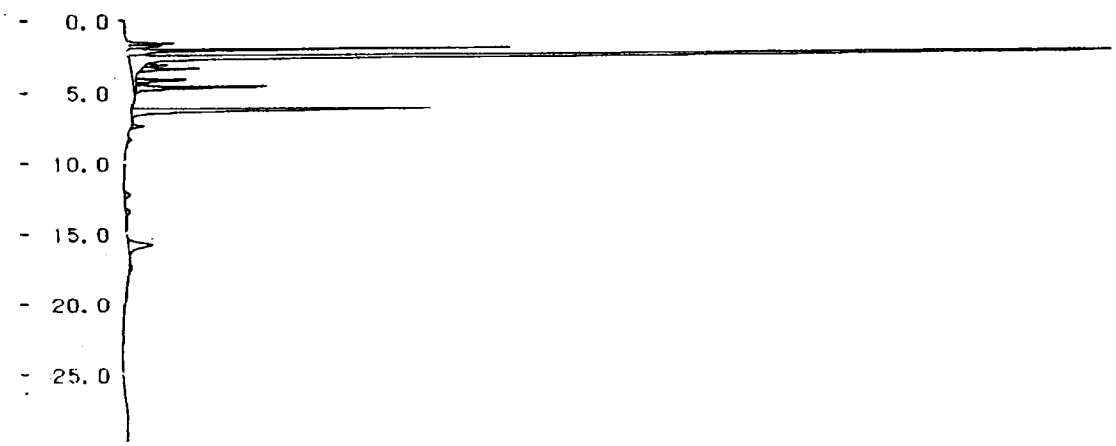

FIG. 2 is a chart showing the result of an HPLC analysis of low purity DM powder (relative purity: 80.3%) which is a starting material.

Figure 3:
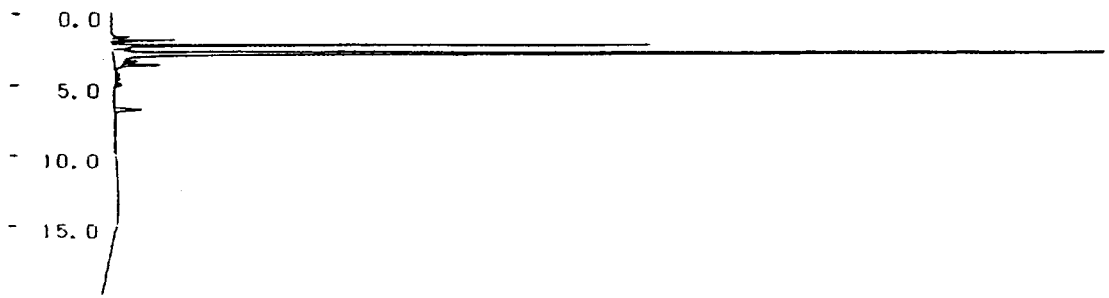

FIG. 3 is a chart showing the result of a solution of DM (relative purity: 88% or more) obtained in Example 5 (present invention).

Figure 4A:
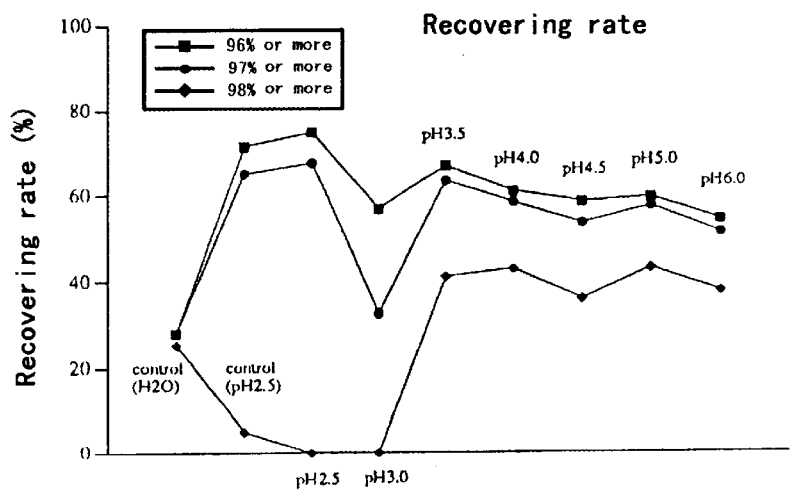
Figure 4B:
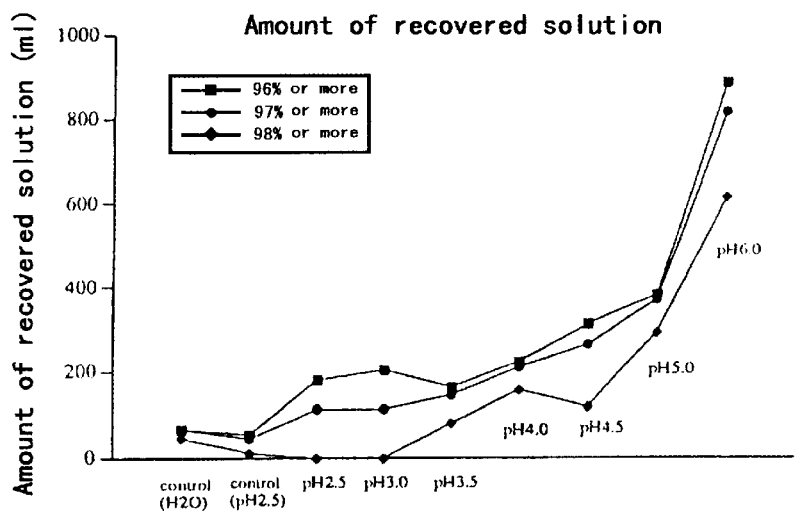
Figure 4C:
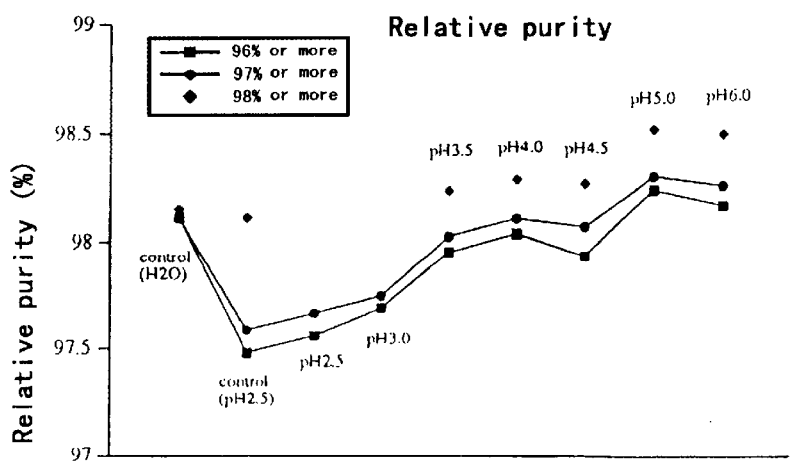

FIGS. 4A to 4C are graphs showing the recovery rates, the recovered liquid amounts and the relative purities of DM in Examples 9 to 17.

Figure 5A:
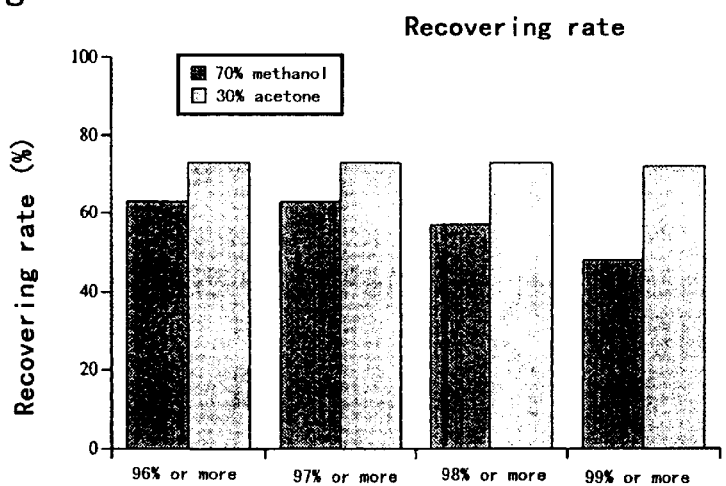
Figure 5B:
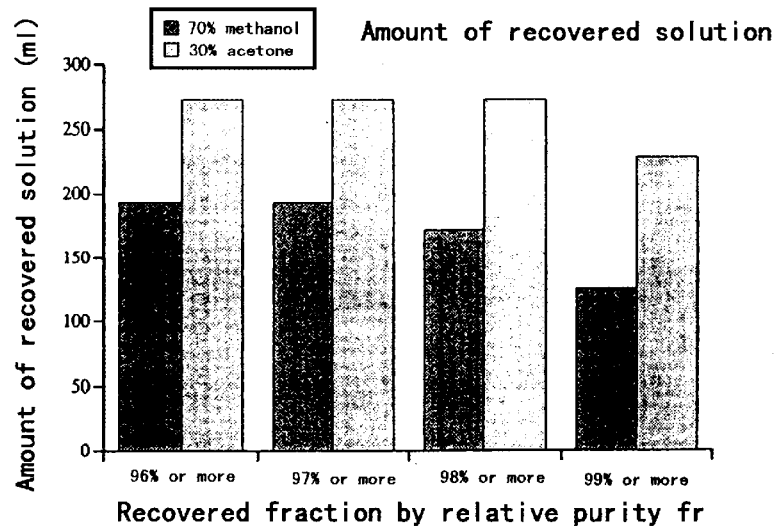
Figure 5C:
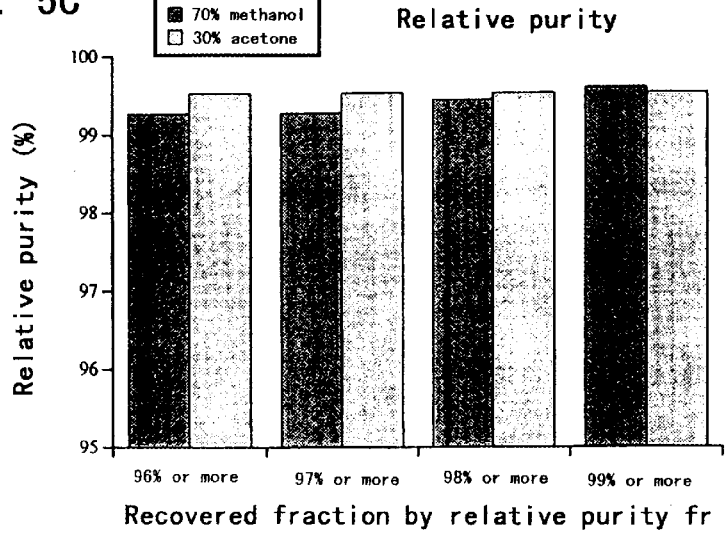

FIGS. 5A to 5C are graphs showing the recovery rates, the recovered liquid amounts and the relative purities of DM in Examples 18 and 19.

Figure 6:
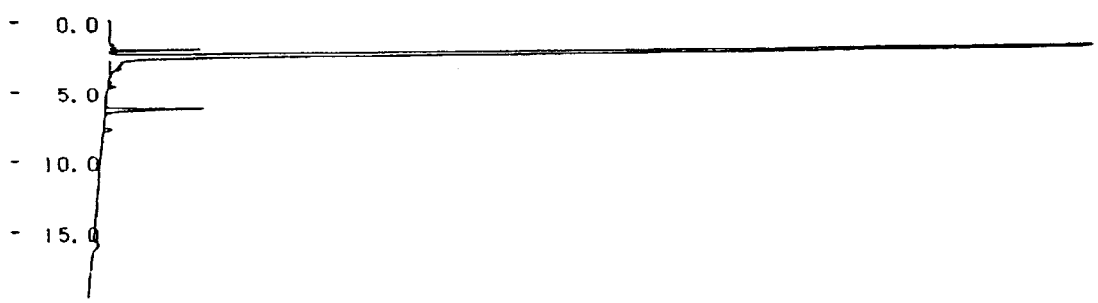

FIG. 6 is an HPLC analysis chart of raw material DM having a higher purity (relative purity: 95.5%) used in Examples 9 to 19.

Figure 7:

FIG. 7 is an HPLC analysis chart of fractions having a relative purity of 98% or more in Examples 9 to 19.

BEST MODE FOR CARRYING OUT THE INVENTION

The crude daunomycin (DM) used in the present invention may have any content of DM as long as clusters and other solid matters are removed from a culture medium containing DM according to a known separating or purifying method and DM is concentrated to some extent. The methods introduced as the conventional techniques described above are included as well in such separating or purifying method, and DM-containing products having a relatively low purity obtained via those methods are included as well. Further, a DM-containing treated product accompanying fixed impurities obtained through a semi-synthetic process, if it corresponds thereto, is included as well in the crude DM used in the present invention.

However, the present invention can more efficiently be applied when DM has a relative purity of about 80% or more, preferably 80 to 96%. The "relative purity" used in the present specification means a proportion of a peak area originating in DM to the whole peak areas showing the elution behaviors of the respective components obtained as result of subjecting the sample to HPLC analysis which shall be described later.

The hydrophobic porous synthetic resin carrier used for adsorbing crude DM may be of any kinds as long as it has functions meeting the object of the present invention and includes, to be specific, a porous polymer obtained by polymerizing styrene with divinylbenzene by a specific method. Such porous polymers are different in a specific surface area and a pore volume depending on the production methods but shall not be restricted by those physical properties as long as the prescribed effects can be obtained by using them in the specific examples of the present invention which shall be described later.

In general, however, the porous polymer having a specific surface area falling in a range of 400 to 800 $m^2/g$ and a pore volume falling in a range of 0.650 to 1.5 ml/g can suitably be used. Such porous polymer can be selected as well from commercially available products and shall not be restricted: Diaion™ HP20 (hereinafter abbreviated as HP20) or HP20SS (hereinafter abbreviated as HP20SS) manufactured by Mitsubishi Chemical Corporation can advantageously be used.

As described above, according to the present invention, DM is eluted from the hydrophobic porous synthetic resin carrier onto which crude daunomycin is adsorbed by using an aqueous solution which contains a water-miscible organic solvent and which is buffered to pH 2.5 to 6. The water-miscible organic solvent shall not specifically be restricted as long as it meets the object of the present invention and includes methanol, ethanol, isopropanol and acetone as a solvent having both a profitability and an elution effect. Among them, methanol and acetone are particularly suited. When such solvents are used, an optimum mixing ratio of these solvents to the aqueous solution is varied depending on the kind of the solvents used and therefore shall not be restricted but, in general, they can be used in a proportion of the solvent to the aqueous solution of 80:20 to 20:80 in terms of a volume basis. For example, when methanol is used, methanol and the aqueous solution can be used in a proportion of 60 to 80/20 to 40, particularly about 70/about 30, and when acetone is used, acetone and the aqueous solution can be used in a proportion of 20 to 40/80 to 60, particularly about 30/about 70.

The aqueous solution containing these solvents has to be buffered particularly to pH 2.5 to 6. In general, the pH of lower than 2.5 tends to reduce the relative purity of DM in the resulting product. On the other hand, the pH exceeding 6 tends to lower the recovering rate of DM. The buffer agent used for buffering may be any buffer agents as long as they do not exert an adverse effect on the product. Such buffer agent shall not be restricted but includes potassium biphthalate-HCl, glycolic acid-HCl, sodium citrate-HCl, potassium citrate-HCl, potassium citrate-citric, acid, succinic acid-$Na_2B_4O_7$, sodium acetate-HCl, sodium acetate-acetic acid, citric acid-$Na_2HPO_4$, tartaric acid-sodium tartarate, lactic acid-sodium lactate, aconitinic acid-NaOH and succinic acid-NaOH. Among them, sodium citrate-HCl is particularly preferred.

The usable concentration of the buffer agent is 0.05M to 1M depending on the kind of the buffer agents used, and in a system of sodium citrate-HCl which is the preferred example, about 0.1M sodium citrate is suitably used.

An operation temperature at which DM adsorbed on the resin carrier described above is eluted therefrom may be any temperature as long as it does not exert an, adverse effect such as degradation on DM or the resin carrier, but it is advantageously in the vicinity of a room temperature (10 to 30° C.). Further, such resin carrier is used usually in the form of a column into which it is charged, but the form shall not be restricted thereto.

In the preparation of the hydrophobic porous synthetic resin carrier onto which crude DM is adsorbed, DM may be adsorbed onto the resin carrier described above by any method as long as it does not exert an adverse effect on the elution described above. To be specific, however, it is prepared preferably by contacting a solution obtained by dissolving crude DM in an acidic aqueous solution (hereinafter referred to as acidic water) having a pH of about 1 to 5 with the carrier described above to thereby adsorb DM onto the carrier and then washing the DM-adsorbed resin carrier with the acidic water described above. The acidic water used for dissolving crude DM may be the same as or different, from the acidic water used for washing the DM-adsorbed resin carrier. The pH of the acidic water may be controlled merely with hydrochloric acid but may be controlled with such buffer agents as described above. A 0.1M citric acid aqueous solution can preferably be used. The pH of the acidic water is controlled particularly preferably to the vicinity of about 2.5. Such washing with the acidic water is continued until impurities are not found to be present in the washing solution. The presence of the impurities in the washing solution can be confirmed by means of, for example, a spectrophotometer.

DM purified by the method of the present invention described above may be treated repeatedly, if necessary, by the preceding method comprising the same or different structure.

Further, in the recovery of DM from the DM-containing fraction purified by the method described above, DM may be recovered from a solution obtained by distilling off the organic solvent by a conventionally known extracting method in which chloroform is used. However, preferred is a method in which the fractions having a relative purity of a fixed value or more are collected; the solution is adjusted to a pH of about 8.5 with sodium hydroxide, and about a half amount of chloroform based on the amount of the solution is added to extract DM; the organic solvent phase is concentrated and dried under reduced pressure, and then al small amount of chloroform/methanol (20:1) is added thereto to dissolve it; and then this solution is added to an excess amount of hexane to precipitate DM, and precipitated DM is filtered, whereby DM having a higher grade can be recovered.

The present invention shall more specifically be explained below with reference to specific examples, but these examples are provided for the purpose of facilitating to understand the present invention and the actions and the effects of the present invention.

EXAMPLE 1 (comparative example)

Purification of Low Purity DM

Figure 1B:
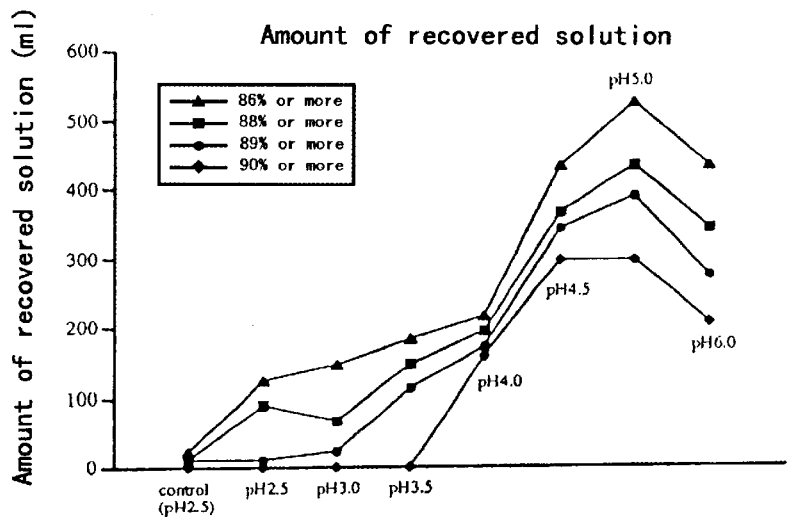
Figure 1C:
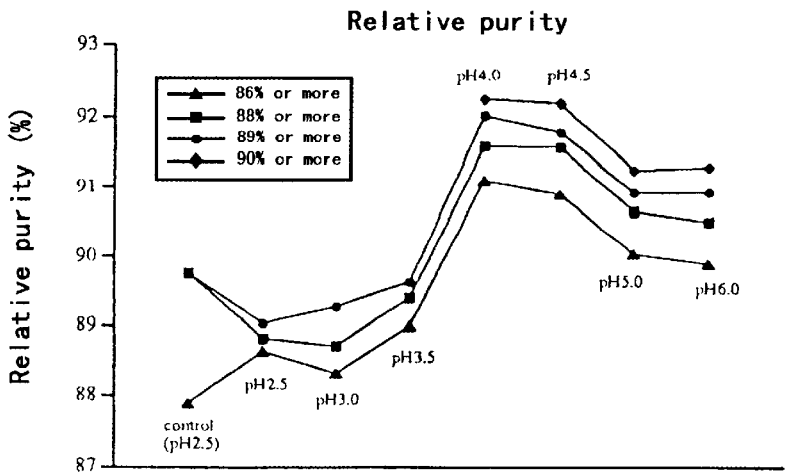

Low purity DM powder of 500 mg (a DM content of 305 mg and a relative purity of 80.3%) was dissolved in 200 ml of acidic water (pH 2.5, HCl), and this solution was passed through an HP20 column (50 ml). After washing the column with 50 ml of the same acidic water, DM was eluted with methanol-acidic water (pH 2.5) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as controls (pH 2.5) in FIGS. 1A to 1C.

HPLC Analytical Conditions:
  Column: ULTRASPHERE ODS, 250×4.6 mm i.d. (Beckman)
  Moving phase: water-acetonitrile (62:38), pH adjusted to 2.2±0.2 with phosphoric acid
  Flow velocity: 1.5 ml/min.
  Detection: 495 nm

EXAMPLE 2 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 2.5), DM was eluted with a methanol-0.1M citric acid buffer solution (pH 2.5) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 2.5 in FIGS. 1A to 1C.

EXAMPLE 3 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 3.0), DM was eluted with a methanol-0.1M citric acid buffer solution (pH 3.0) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 3.0 in FIGS. 1A to 1C.

EXAMPLE 4 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 3.5), DM was eluted with a methanol-0.1M citric acid buffer solution (pH 3.5) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 3.5 in FIGS. 1A to 1C.

EXAMPLE 5 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 4.0), DM was eluted with a methanol-0.1M citric acid buffer solution (pH 4.0) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 4.0 in FIGS. 1A to 1C. The HPLC analysis charts of low purity DM used as the raw material and a solution obtained by sampling the DM fractions having a relative purity of 88% or more are shown in FIG. 2 and FIG. 3 respectively.

EXAMPLE 6 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 4.5), DM was eluted with a methanol-0.1M citric acid buffer solution (pH 4.5) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 4.5 in FIGS. 1A to 1C.

EXAMPLE 7 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 5.0), DM was eluted with a methanol-0.1M citric acid buffer solution (pH 5.0) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 5.0 in FIGS. 1A to 1C.

EXAMPLE 8 (present invention)

Purification of Low Purity DM

Low purity DM powder of 500 mg (a DM content of 305 mg and a relative purity of 80.3%) was dissolved in 200 ml of acidic water (pH 2.5, HCl), and this solution was passed through the HP20 column (50 ml). After washing the column with 50 ml of the same acidic water and 100 ml of a 0.1M citric acid buffer solution (pH 6.0), DM was eluted with a methanol-0.1M citric acid buffer solution (pH 6.0) (70:30), and the DM-eluted fractions were subjected to HPLC analysis. The DM fractions having relative purities of 86, 88, 89 and 90% or more were sampled respectively, and the recovering rates, the amounts of the recovered solutions and the relative purities of DM are shown as pH 6.0 in FIGS. 1A to 1C.

EXAMPLE 9 (comparative example)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of water, DM was eluted with methanol-water (70:30), and the DM-eluted fractions were subjected to HPLC analysis. The DM fractions having relative purities of 96, 97 and 98% or more were sampled respectively, and the recovering rates, the amounts (if the recovered solutions and the relative purities of DM are shown as controls (H20) in FIGS. 4A to 4C.

EXAMPLE 10 (comparative example)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water, DM was eluted with methanol-acidic water (pH 2.5) (70:30), and the DM-eluted fractions were subjected to HPLC analysis. The DM fractions having relative purities of 96, 97 and 98% or more were sampled respectively, and the recovering rates, the amounts of the recovered solutions and the relative purities of DM are shown as controls (pH 2.5) in FIGS. 4A to 4C.

EXAMPLE 11 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 2.5), DM was eluted with a methanol-0.1M citric acid buffer solution (pH 2.5) (70:30), and the DM-eluted fractions were subjected to HPLC analysis. The DM fractions having relative purities of 96, 97 and 98% or more were sampled respectively, and the recovering rates, the amounts of the recovered solutions and the relative purities of DM are shown as pH 2.5 in FIGS. 4A to 4C.

EXAMPLE 12 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 3.0), DM was eluted with a methanol-0.1M citric acid buffer solution (pH 3.0) (70:30). The DM-eluted fractions having a relative purity of 98% or more were sampled and subjected to HPLC analysis. The DM fractions having relative purities of 96, 97 and 98% or more were sampled, respectively, and the recovering rates, the amounts of the recovered solutions and the relative purities of DM are shown as pH 3.0 in FIGS. 4A to 4C.

EXAMPLE 13 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 3.5), DM was eluted with a methanol-0.1M citric acid buffer solution (pH 3.5) (70:30), and the DM-eluted fractions were subjected to HPLC analysis. This experiment was carried out twice. The DM fractions having relative purities of 96, 97 and 98% or more were sampled respectively, and the recovering rates, the amounts of the recovered solutions and the relative purities of DM are shown as pH 3.5 in FIGS. 4A to 4C.

EXAMPLE 14 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 4.0), DM was eluted with a methanol-0.1M citric acid buffer solution (pH 4.0) (70:30), and the DM-eluted fractions were subjected to HPLC analysis. This experiment was carried out twice. The DM fractions having relative purities of 96, 97 and 98% or more were sampled respectively, and the recovering rates, the amounts of the recovered solutions and the relative purities of DM are shown as pH 4.0 in FIGS. 4A to 4C.

EXAMPLE 15 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 4.5), DM was eluted with a methanol-0.1M citric acid buffer solution (pH 4.5) (70:30), and the DM-eluted fractions were subjected to HPLC analysis. This experiment was carried out twice. The DM fractions having relative purities of 96, 97 and 98% or more were sampled respectively, and the recovering rates, the amounts of the recovered solutions and the relative purities of DM are shown as pH 4.5 in FIGS. 4A to 4C.

EXAMPLE 16 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 5.0), DM was eluted with a methanol-0.1M citric acid buffer solution (pH 5.0) (70:30), and the DM-eluted fractions were subjected to HPLC analysis. This experiment was carried out twice. The DM fractions having relative purities of 96, 97 and 98% or more were sampled respectively, and the recovering rates, the amounts of the recovered solutions and the relative purities of DM are shown as pH 5.0 in FIGS. 4A to 4C.

EXAMPLE 17 (present invention)

Purification of Raw Material DM Having a Higher Purity

Raw material DM powder of 500 mg having a higher purity (a DM content of 463 mg and, a relative purity of 98.8%) was dissolved in 10 ml of acidic water (pH 2.5, HCl), and this solution was passed through the HP20 column (50 ml). After washing the column with 50 ml of the same acidic water and 100 ml of a 0.1M citric acid buffer solution (pH 6.0), DM was eluted with a methanol-0.1M citric acid buffer solution (pH 6.0) (70:30), and the DM-eluted fractions were subjected to HPLC analysis. The DM fractions having relative purities of 96, 97 and 98% or more were sampled respectively, and the recovering rates, the amounts of the recovered solutions and the relative purities of DM are shown as; pH 6.0 in FIGS. 4A to 4C.

EXAMPLE 18 (present invention)

Purification of Raw Material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through an HP20SS column (50 ml). After washing the column with 50 ml of the same acidic water and 100 ml of a 0.1M citric acid buffer solution (pH 4.0), DM was eluted with a methanol-0.1M citric acid buffer solution (pH 4.0) (70:30), and the DM-eluted fractions were subjected to HPLC analysis. The DM fractions having relative purities of 96, 97, 98 and 99% or more were sampled respectively, and the recovering rates, the amounts of the recovered solutions and the relative purities of DM are shown in the form of a black bar in FIGS. 5A to 5C.

EXAMPLE 19 (present invention)

Purification of raw material DM Having a Higher Purity

Raw material DM powder of 500 mg having a higher purity (a DM content of 463 mg and a relative purity of 98.8%) was dissolved in 10 ml of acidic water (pH 2.5, HCl), and this solution was passed through he HP20SS column (50 ml). After washing the column with 50 ml of the same acidic water and 100 ml of a 0.1M citric acid buffer solution (pH 4.0), DM was eluted with an acetone-0.1M citric acid buffer solution (pH 4.0) (30:70), and the DM-eluted fractions were subjected to HPLC analysis. The DM fractions having relative purities of 96, 97, 98 and 99% or more were sampled respectively, and the recovering rates, the amounts of the recovered solutions and the relative purities of DM are shown in the form of a void bar in FIGS. 5A to 5C.

The HPLC analysis charts of raw material DM having a higher purity used as the raw material and a solution obtained by sampling the DM fractions having a relative purity of 98% or more are shown in FIG. 6 and FIG. 7 respectively.

EXAMPLE 20 (present invention)

Recovery of Purified DM

DM was recovered from the solution obtained by sampling the DM fractions having a relative purity of 98% or more in Example 18. The sampled solution was adjusted to a pH of 8.5 with 4N sodium hydroxide, and about a half amount of chloroform based on the amount of the solution was added to extract DM. The organic solvent phase containing DM was concentrated and dried under reduced pressure, and then a small amount of chloroform/methanol (20:1) was added thereto to dissolve it. This solution was added to an excess amount of hexane, and precipitated DM was filtered and dried. at 40° C. under reduced pressure for one night. In this case, the resulting DM powder had a yield of 242 mg.

It can be found from the examples described above that according to FIGS. 1A to 1C, the method of the present invention can provide the products having a higher relative purity at a higher recovering rate as compared with those of the controls (comparative examples). To be specific, in the comparative example, the fractions having a relative purity of 89% or more (black circles and rhomboids) are not obtained, and the fraction having a relative purity of 88% or more (black quadrangles) has as low recovering rate as 10% or less, but in the method-of the present invention, for example, pH 2.5, the fraction having a relative purity of 88% or more has a recovering rate exceeding 65%, and the fraction having a relative purity of 89% or more also has a recovering rate exceeding 10%. Further, in pH 5.98 according to the present invention, even the fraction having a relative purity of 90% or more (black rhomboid) has a recovering rate exceeding 15%. These tendencies are observed likewise when acetone is used as the water-miscible organic solvent (refer to FIGS. 5A to 5C).

What is claimed is:

1. A purifying method of daunomycin comprising:

eluting daunomycin from a hydrophobic porous synthetic resin carrier, wherein daunomycin is adsorbed onto said resin carrier from crude daunomycin, with an eluting buffered aqueous solution containing a water-miscible organic solvent which is buffered to a pH of about 3.25 to 6, and recovering purified daunomycin having a relative purity of at least 98% from the eluate;

wherein said organic solvent is at least one solvent selected from the group consisting of methanol and ethanol.

2. The purifying method as described in claim 1, wherein the hydrophobic porous synthetic resin carrier onto which crude daunomycin is adsorbed is prepared by:

contacting a solution obtained by dissolving crude daunomycin in an acidic aqueous solution having a pH of about 1 to 5 with the hydrophobic porous synthetic resin carrier to thereby adsorb daunomycin on the resin carrier; and washing the resin carrier adsorbing daunomycin with said acidic aqueous solution having a pH of about 1 to 5.

3. The purifying method as described in claim 2, wherein said acidic aqueous solution used for washing the carrier adsorbing daunomycin is buffered.

4. The purifying method as described in claim 1, wherein said eluting buffered aqueous solution containing the organic solvent is buffered with a citric acid buffer solution, and said organic solvent is methanol.

5. The purifying method as described in claim 1, wherein said eluting buffered aqueous solution containing the organic solvent has a volume ratio of the organic solvent to the aqueous solution of 80:20 to 20:80.

6. The purifying method as described in claim 1, wherein the crude daunomycin has a relative purity of at least about 95%.

7. A purifying method of daunomycin comprising:
eluting daunomycin from a hydrophobic porous synthetic resin carrier, wherein daunomycin is adsorbed onto said resin carrier from crude daunomycin, with an aqueous solution containing a water-miscible organic solvent which is buffered to a pH of about 2.5 to about 5.5, and
recovering purified daunomycin having a relative purity is 80% or more from the eluate;
wherein said organic solvent is at least one solvent selected from the group consisting of methanol and ethanol.

8. The purifying method as described in claim 7, wherein crude daunomycin has a relative purity of 80 to 86%.

9. The purifying method as described in claim 7, wherein crude daunomycin has a relative purity of 86% or more.

10. The purifying method as described in claim 7, wherein crude daunomycin has a relative purity of 88% or more.

* * * * *